United States Patent
Bardill et al.

(10) Patent No.: US 9,198,781 B2
(45) Date of Patent: Dec. 1, 2015

(54) IMPLANT, SYSTEM FORMED OF AN IMPLANT AND A CATHETER, AND METHOD FOR PRODUCING SUCH A SYSTEM

(71) Applicant: BIOTRONIK AG, Buelach (CH)

(72) Inventors: Anita Bardill, Zurich (CH); Adrian Blaser, Zurich (CH); Aldo Jakob, Eglisau (CH)

(73) Assignee: BIOTRONIK AG, Beulach (CH)

( * ) Notice: Subject to any disclaimer, the term of this patent is extended or adjusted under 35 U.S.C. 154(b) by 0 days.

(21) Appl. No.: 14/021,937

(22) Filed: Sep. 9, 2013

(65) Prior Publication Data

US 2014/0081375 A1   Mar. 20, 2014

Related U.S. Application Data

(60) Provisional application No. 61/703,278, filed on Sep. 20, 2012.

(51) Int. Cl.
| | |
|---|---|
| *A61F 2/06* | (2013.01) |
| *A61F 2/82* | (2013.01) |
| *A61F 2/95* | (2013.01) |
| *A61F 2/966* | (2013.01) |
| A61F 2/24 | (2006.01) |
| A61F 2/00 | (2006.01) |

(52) U.S. Cl.
CPC ... *A61F 2/82* (2013.01); *A61F 2/95* (2013.01); *A61F 2/966* (2013.01); *A61F 2/0095* (2013.01); *A61F 2/2418* (2013.01); *A61F 2002/9665* (2013.01); *A61F 2250/006* (2013.01); *Y10T 29/49826* (2015.01)

(58) Field of Classification Search
CPC ..... A61F 2002/9505; A61F 2/95; A61F 2/82; A61F 2/966; A61F 2002/9665
USPC ............ 623/1.11, 1.12, 1.2; 600/200; 29/235, 29/270, 272, 282, 283.5
See application file for complete search history.

(56) References Cited

U.S. PATENT DOCUMENTS

| | | | | |
|---|---|---|---|---|
| 5,026,377 | A | * | 6/1991 | Burton et al. ................. 606/108 |
| 5,928,258 | A | * | 7/1999 | Khan et al. .................... 606/191 |
| 6,019,778 | A | * | 2/2000 | Wilson et al. ................ 606/198 |
| 6,090,035 | A | * | 7/2000 | Campbell et al. ................ 600/7 |
| 6,149,680 | A | * | 11/2000 | Shelso et al. ................ 623/1.11 |
| 2005/0065590 | A1 | * | 3/2005 | Shelso ......................... 623/1.11 |

(Continued)

FOREIGN PATENT DOCUMENTS

WO    WO 2009134801 A2 * 11/2009 ................ A61F 2/84

*Primary Examiner* — Todd E Manahan
*Assistant Examiner* — Charles Wei
(74) *Attorney, Agent, or Firm* — Wagenknecht IP Law Group PC

(57) ABSTRACT

An implant (10, 10', 10", 10'''), in particular an intraluminal endoprosthesis, with an open-worked, hollow cylindrical and/or hollow conical main structure (11), wherein the main structure (11) can adopt a compressed state or an expanded state. To simplify final assembly by the doctor, a first tubular shaft (16, 16') is additionally provided, on the outer face of which the main structure (11) is arranged in the compressed state, at least in portion, wherein the first shaft (16, 16') has a first connection portion (20, 23), with which the first shaft (16, 16') can be connected to the inner shaft (32, 32', 32a, 32b) of a catheter (30, 30', 30"). A corresponding system formed of an implant of this type and of a catheter (30, 30', 30") and a method for producing such a system.

17 Claims, 5 Drawing Sheets

(56) References Cited

U.S. PATENT DOCUMENTS

| | | |
|---|---|---|
| 2006/0276872 A1* | 12/2006 | Arbefeuille et al. .......... 623/1.11 |
| 2007/0270932 A1* | 11/2007 | Headley et al. .............. 623/1.11 |
| 2010/0298931 A1* | 11/2010 | Quadri et al. ................. 623/2.11 |
| 2011/0046712 A1* | 2/2011 | Melsheimer et al. ......... 623/1.11 |
| 2011/0208296 A1* | 8/2011 | Duffy et al. ................... 623/2.11 |
| 2011/0224774 A1* | 9/2011 | Silveira et al. ............... 623/1.11 |

* cited by examiner

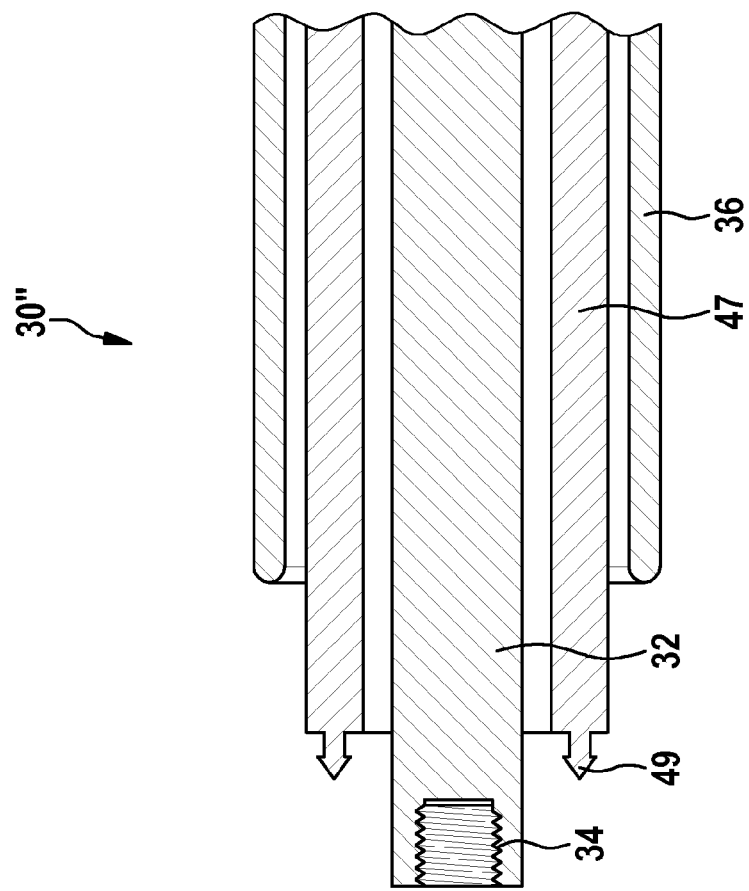
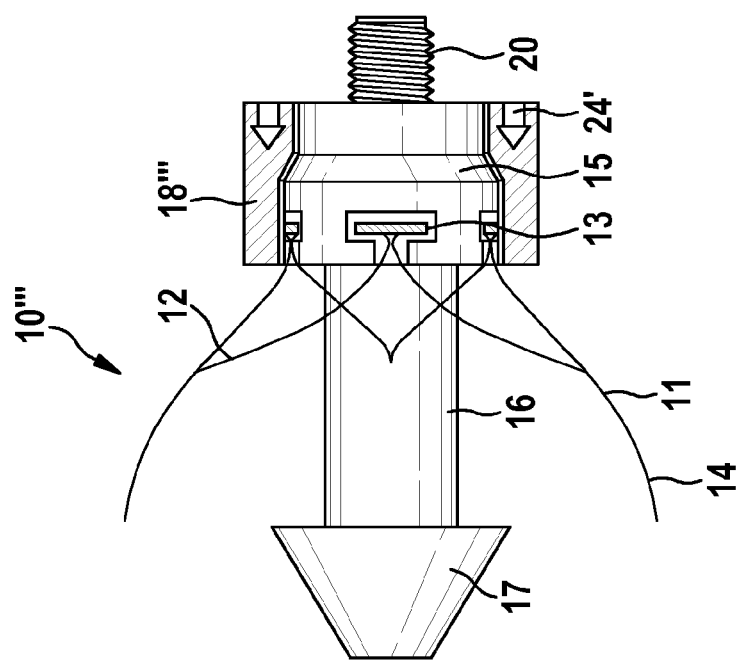
FIG. 6

IMPLANT, SYSTEM FORMED OF AN IMPLANT AND A CATHETER, AND METHOD FOR PRODUCING SUCH A SYSTEM

CROSS REFERENCE TO RELATED APPLICATIONS

This application claims benefit of priority to U.S. patent application Ser. No. 61/703,278, filed Sep. 20, 2012; the content of which is herein incorporated by reference in its entirety.

TECHNICAL FIELD

The present invention relates to an implant, in particular an intraluminal endoprosthesis, with an open-worked, hollow cylindrical and/or hollow conical main structure, wherein the main structure can adopt a compressed state and an expanded state. The invention further relates to a system for introducing an implant, preferably an intraluminal endoprosthesis, into a bodily cavity, the system consisting of the above-described implant and a catheter. In addition, the invention relates to a method for producing a system of this type.

BACKGROUND

A wide variety of medical implants, in particular intraluminal endoprostheses, are known from the prior art for a wide range of applications. Within the context of the present invention, implants are to be understood to be endovascular prostheses or other endoprostheses, for example stents (vessel stents (vascular stents, including stents for application in the area of the heart and heart valve stents, for example mitral valve stents and pulmonary valve stents) and bile duct stents), endoprostheses for closing patent foramen ovale (PFO), stent grafts for treating aneurisms, endoprostheses for closing an ASD (atrial septal defect) and prostheses in the area of hard and soft tissue. An implant of this type is often inserted by means of a catheter into the organ or vessel to be treated.

Stents and other endovascular endoprostheses have an open-worked hollow cylindrical (tubular) and/or hollow conical main structure, which is open at both longitudinal ends, wherein the main structure is often composed of a multiplicity of crosspieces. In a main structure of this type, for example in the case of a heart valve stent, valvular cusps, for example three valvular cusps, may be arranged on the inner side and form the heart valve and may consist of a plastics or of a biological material, for example porcine pericardium. The stent carries the heart valve and anchors it in the heart.

Catheters are small pipes or tubes of different diameter, which can be introduced into the respective bodily cavity to be treated. During treatment with a catheter, a guide wire and possibly a guide catheter is/are first introduced into the organ or vessel to be treated. The catheter is then advanced along the guide wire as far as the point of the organ or vessel to be treated, so that the implant arranged on the catheter is placed in the region of the point of the organ or vessel to be treated. The implant is then decoupled from the catheter and possibly dilated. The catheter is then removed. The guide wire is also withdrawn from the organ or vessel, either at the same time or subsequently. A catheter that has an inner shaft and an outer shaft is often used to insert a stent.

Stents and other implants normally adopt two states: namely a compressed state with a small diameter and an expanded state with a larger diameter. In the compressed state, the implant can be introduced into the vessel or organ to be treated, through narrow vessels, by means of a catheter and can be positioned at the point to be treated. To this end, the implant is crimped onto the balloon of a catheter for example and is thus transferred into the compressed state. The implant is then dilated at the treatment location, for example by means of the balloon of the catheter, and then adopts the expanded state, in which the implant remains in the vessel or organ and is fixed there, after which the catheter is withdrawn again from the body of the patient being treated. Alternatively, if the main structure of an implant consists of a self-expanding material (for example Nitinol), said implant adopts the compressed state as result of compression below the transition point and adopts the expanded state above the transition point.

A heart valve prosthesis and a deflecting device are known from document U.S. Pat. No. 8,029,564 B2. The system further includes a line, which is passed through the free ends of the stent posts, which carry the heart valve. The stent posts can be bent inwardly by means of this line so as to achieve a closed state. This system, however, is not suitable for non-invasive transfer by means of a catheter to the point to be treated, since it is too bulky in the foot region.

With heart valve stents that can be transported by means of a catheter to the point to be treated, for example the COREVALVE transcatheter heart valve of Medtronic GmbH, complex assembly of the stent is first necessary before the non-invasive intervention so as to assemble said stent on the catheter. Five different tools are currently used for this purpose. The procedure, which is generally carried out by the doctor, is very complex and therefore is highly susceptible to failure.

There is also the problem in the known systems that the sent retention force may be insufficient. This means that the ends of a stent arranged on the catheter may spring out from the fixing in a curve of a vessel through which the system is guided on the way to the bodily cavity to be treated. If this happens, the stent may be placed inaccurately at the location to be treated or it may be necessary to re-crimp or re-capture the stent with the catheter, which is extremely difficult to implement.

SUMMARY

The object is therefore to create an implant that makes it possible to simplify the stent assembly process. Furthermore, the stent will be better fixed on the catheter so as to prevent it from springing out from the anchoring. A further object is to create a corresponding system formed of a catheter and implant. Another object is to specify a method for producing a system formed of a catheter and an intraluminal endoprosthesis, said method being practicable in a simple manner and having a low risk of error.

The above object is achieved by an implant having the features of claim 1. In particular, the implant according to the invention is additionally provided with a first tubular shaft, on the outer face of which the main structure of the implant is arranged in the compressed state, at least in portion, wherein the first shaft has a first connection portion, with which the first shaft can be connected to the inner shaft of a catheter.

In the form of the first shaft, the implant according to the invention already contains, to a certain extent, a part of the inner shaft of the catheter, with which the implant is then transported to the point to be treated. However, this function is only performed by the first shaft when the inner shaft of the catheter is connected to the first shaft. The inventors have discovered in particular that, in the case of the preassembly of the implant on a decoupled distal inner shaft portion (corresponding to the first shaft) carried out in accordance with the invention, some of the complex and difficult process steps when initially fixing the implant no longer have to be carried out by the doctor, but can instead be completed by the manufacturer under standardized conditions. The risk of severe unfolding of an implant fixed incorrectly by a doctor on the catheter is thus minimized. The number of steps involved in the assembly process carried out by the doctor is thus reduced and the process steps are simplified and user-friendlier. The preassembled implant may optionally advantageously be stored without difficulty in the necessary fluid until its use. In the case of a heart valve stent, the portion that is compressed in the preassembled state when arranged on the first shaft is preferably arranged at the proximal end of the stent without vascular cusps, thus ensuring that the heart valve material (pericardium or plastics) can be stored in the unfolded state.

The connection to the inner shaft of the catheter through the first connection portion of the first shaft can be achieved by means of any non-positive, positive and/or bonded connection, for example with a bayonet closure, a thread or an adhesive. The connection can be releasable or non-releasable.

In an exemplary embodiment, a second shaft that is tubular at least in portion is provided in addition to the implant and is arranged, preferably at its proximal end, so as to surround the main structure. The second shaft preferably surrounds the main structure in the portion in which the implant is arranged on the first shaft in the compressed state. The implant is fixed on the first shaft by the manufacturer by means of the second shaft and is fixed on the catheter once the first shaft has been connected to the inner shaft of the catheter. An increased implant retention force is thus achieved, and therefore the implant is better fixed on the catheter in the curve of a vessel and does not spring out. The implant can thus be placed more precisely at the treatment location and re-crimping or re-capturing of the implant is not necessary. The second shaft can alternatively also be used to pre-crimp the main structure before fixing to an outer shaft.

In accordance with a development of the invention, means for fixing the second shaft in the proximal direction are additionally provided, for example a proximally arranged cover or a pin arranged at the proximal end of the second shaft and protruding in the radial direction. Due to the main lattice of the implant, a force is exerted specifically on the second shaft, which leads to a displacement of the shaft in the proximal direction. The second shaft can thus slide from the implant. The means for fixing, for example a cover or a pin protruding in the radial direction, which is arranged at the proximal end of the second shaft, act against the force exerted by the main lattice onto the second shaft. Further reversible positive or non-positive fit techniques can also be used for this fixing operation.

In accordance with a further exemplary embodiment, the second shaft has a conical portion that is preferably arranged at the distal end of the second shaft. The part of the main lattice arranged on the distal side of the second shaft can be better crimped during assembly of the implant as a result of this portion.

It is also advantageous if the second shaft has a connection portion, with which the second shaft can be connected to a tubular outer shaft or a tubular fixing shaft (auxiliary shaft) of the catheter. The connection to the outer shaft or the fixing shaft of the catheter can be formed in principle by any non-positive, positive or bonded connection and can be either releasable or non-releasable. In this exemplary embodiment, the crimping is carried out during assembly of the implant by displacing the outer shaft in the distal direction. The optionally additionally provided fixing shaft arranged between the inner shaft and outer shaft is used to hold the implant at the desired point on the inner shaft of the catheter or on the first shaft detached from the outer shaft, that is to say independently, even if curves in the vessels have to be traversed during transport to the point in the body to be treated. The fixing of the main structure by the fixing shaft can be released once the implant has been successfully placed at the desired point, for example by the treating doctor in a separate step, that is to say detached from the outer shaft.

When the implant is assembled on the catheter, there is also the problem that the tip of the catheter may have such a large outer diameter that an auxiliary tube, for example in the form of a second shaft, cannot be slid over the tip for crimping. In this case, it is advantageous if the inner shaft of the catheter is formed in two parts and, accordingly, if the first shaft, preferably at its distal end, has a second connection portion to which the first shaft can be connected to the distal tip of the inner shaft of a catheter. The first shaft is then only connected to the catheter tip or to the second part of the inner shaft after the crimping process. The connection between the second connection portion of the first shaft and the second part of the inner shaft of the catheter may also again be formed as any desired non-positive, positive and/or bonded connection and may be releasable or non-releasable.

The above object is also achieved with the above-mentioned advantages by a system for introducing an implant, in which the inner shaft of the catheter has a connection portion, preferably arranged at its distal end, with which the inner shaft can be connected to the first shaft of the implant. In this case, the implant corresponds to one of the embodiments disclosed above.

The advantages of the system according to the invention have already been explained in conjunction with the implant according to the invention.

In a preferred exemplary embodiment, the outer shaft of the catheter or the fixing shaft of the catheter has a connection portion, preferably arranged at the respective distal end, with which the outer shaft or the fixing shaft respectively can be connected to the second shaft of the implant. As already explained above, the fixing shaft of the catheter can be used to fix the implant independently.

The inner shaft of the catheter is preferably formed in two parts, wherein the first part is formed by a proximal portion of the inner shaft and the second part is formed by a distal portion of the inner shaft. The distal portion contains the catheter tip in particular, which is of significant importance in terms of the insertion of the system according to the invention into the body, since it constitutes the first element of the catheter, after the guide wire, to penetrate the body and is located in a guiding position during movement of the catheter through the body.

The above object is also achieved by a method in which the first connection portion of the first shaft is connected to the opposed connection portion of the inner shaft of the catheter before the system is introduced into a bodily cavity of a human or animal. This method constitutes a simple possibility for producing a system consisting of a catheter and an implant. The method according to the invention includes fewer process steps to be carried out by a doctor compared to the conventional method and therefore in particular facilitates his activity before implantation. Once the first shaft has been connected to the inner shaft of the catheter, the main body can then be pre-crimped, for example by means of a second shaft that is advanced distally. The outer shaft, which may follow directly proximally behind the second shaft, is then guided over the implant. The second shaft is then slid distally over the catheter tip and is removed from the instrument. Further embodiments will be explained below in the exemplary embodiments.

With a two-part embodiment of the inner shaft, the first connection portion of the first shaft is connected to the opposed connection portion of the first part of the inner shaft of the catheter and the second connection shaft of the first shaft is connected to the opposed connection portion of the second part of the inner shaft of the catheter before the system is introduced into a bodily cavity of a human or animal. As has already been explained above, this embodiment is of particular significance if a second shaft for pre-crimping the implant is dimensioned in such a way that the respective shaft cannot be slid over the catheter tip. In this case, the main lattice is first pre-crimped by means of the second shaft once the first part of the inner shaft has been connected to the first shaft, and is then removed from the implant. The second part of the inner shaft is then connected to the second connection portion of the first shaft.

It is further advantageous if the connection portion of the second shaft is connected to the opposed connection portion of the outer shaft of the catheter or to the opposed connection portion of the fixing shaft of the catheter. In the first case, the outer shaft of the catheter as well as the second shaft connected previously thereto is used to crimp the main lattice, whereas in the second case the main lattice is fixed by the second shaft.

Further objectives, features, advantages and possibilities for application of the invention will become clear from the following description of exemplary embodiments of the invention on the basis of the figures. All described features and/or those illustrated in the figures form part of the subject of the present invention, both alone and in any combination and irrespective of the summary thereof in the individual claims or back-references of the claims.

DETAILED DESCRIPTION

The figures show the exemplary embodiments in schematic and simplified form and, in particular, illustrate the details that are important for comprehending the invention. Details that are insignificant to the invention have been left out in some instances. Furthermore, in conjunction with the present invention, the designation "distal end" means the end of the implant or of the catheter that points away from the treating doctor during introduction of the implant into the body, whereas the "proximal end" points toward the person operating the catheter.

Figure 1:
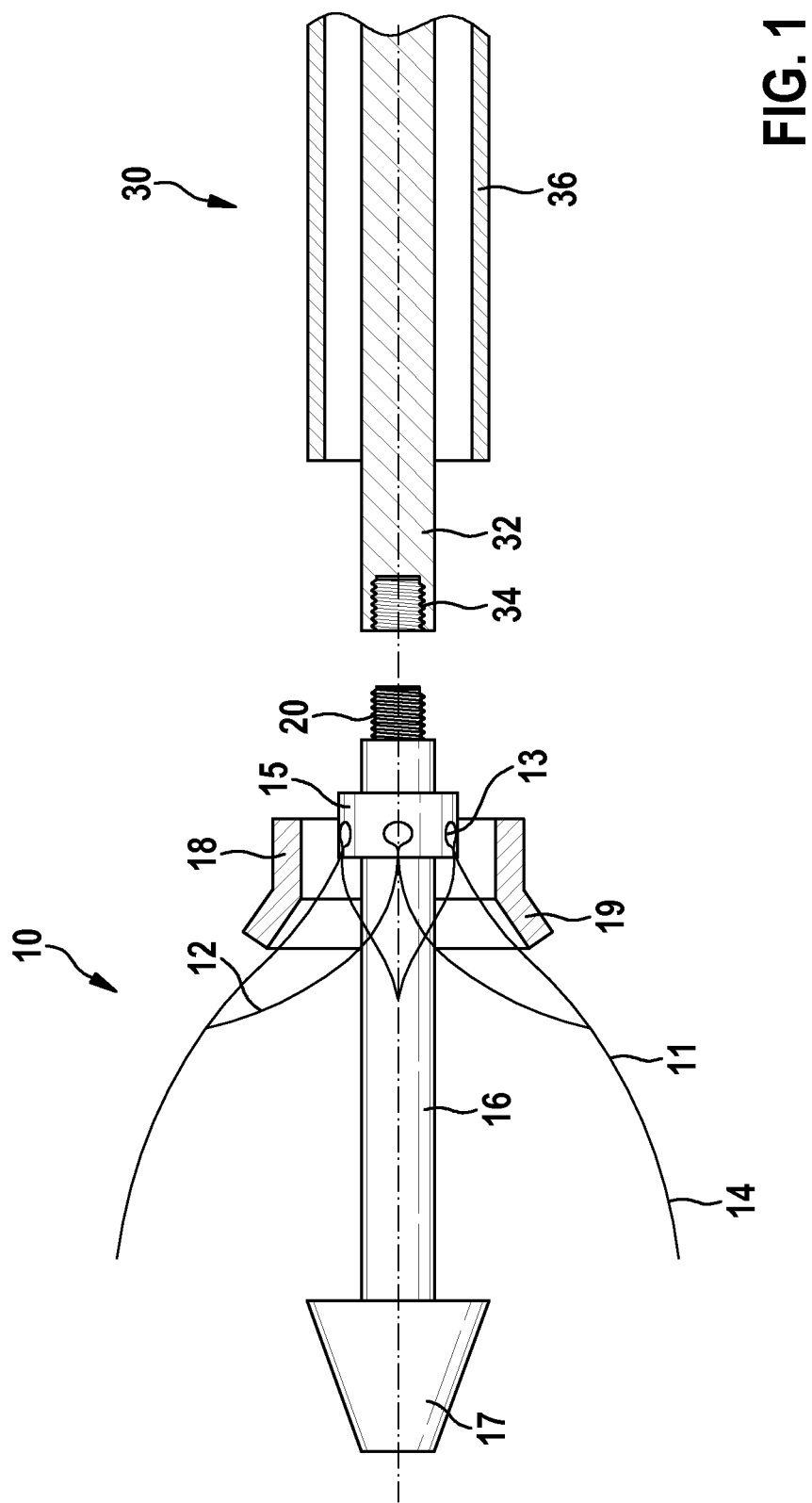
FIG. 1 shows a cross-sectional view of a first exemplary embodiment of a system according to the invention with a first exemplary embodiment of an implant according to the invention.

FIG. 1 illustrates the first exemplary embodiment, in the as yet unassembled state, of a system according to the invention with an implant according to the invention, the implant being formed as a heart valve stent 10, and with a catheter 30. The implant 10 according to the invention has a main structure 11, which is open-worked and preferably consists of a multiplicity of crosspieces, which produce a mesh structure. The main structure 11, which is open at both ends, has a hollow cylindrical portion at its proximal end 13 and a hollow conical portion at its distal end 14. In the inner region enclosed by the main structure 11, the heart valve stent 10 preferably has three valvular cusps 12, which form the heart valve and, for example, each consist of a biological material, for example porcine pericardium. The valvular cusps may alternatively be formed from a plastic. The main structure 11 is compressed at the proximal end 13 of the heart valve stent, whereas the main structure 11 is present in the expanded state at the distal end 14 thereof. In this case, the main structure 11 is fastened in a ring 15 at its outermost proximal end 13. For this purpose, loop-shaped rings or T-shaped elements are formed at the outermost proximal end 13 on the main structure 11 and fit into corresponding recesses in the ring 15.

The main structure 11 of the heart valve stent 10, which consists for example of a self-expanding material (for example Nitinol), is arranged on a first shaft 16, which is formed by a hollow cylindrical tube. A ring 15 with recesses is fixed in the proximal portion of the first shaft 16. The main structure 11 is attached to the first shaft 16 by coupling the loop-shaped rings or T-shaped elements at the outermost proximal end 13 of the main structure 11 into the corresponding recesses in the ring 15. A conically extending portion 17 is provided at the distal end of the first shaft 16 and forms the tip of the catheter 30 after connection of the first shaft 16 to the inner shaft 32 of the catheter 30. To this end, the cone is arranged such that the end with the smaller diameter lies at the distal end of the first shaft 16.

At the proximal end 13 of the main structure 11, a second shaft 18 arranged on the main structure 11 is also provided, which has a conical portion 19 at its distal end. For example, the second shaft 18 prevents the main structure 11 of a heart valve stent 10 consisting of a self-expanding material from opening, whereby said main structure would detach from the first shaft 16. At its proximal end, the first shaft 16 has a first connection portion 20, on which an outer thread for example is formed.

When the system is assembled, the catheter 30, that is to say in particular a connection portion 34 of the inner shaft 32, which for example has an inner thread, is engaged with the outer thread of the first connection portion 20 of the first shaft in such a way that the inner shaft 32 of the catheter 30 is connected to the first shaft 16 of the implant. The second shaft 18 is then displaced in the distal direction so as to crimp the main structure 11 with the valvular cusps 12. The outer shaft 36 is then moved over the crimped heart valve stent 10, likewise in the distal direction, and the second shaft 18 is removed from the instrument, wherein, to this end, the second shaft 18 is slid over the conical portion 17 of the first shaft 16.

As alternative possibilities for interconnecting the first shaft 16 and the inner shaft 32 of the catheter 30 in the respective connection portions 20, 34, the uses of a bayonet closure or of adhesive (instant adhesive) are also considered for example.

Figure 2:
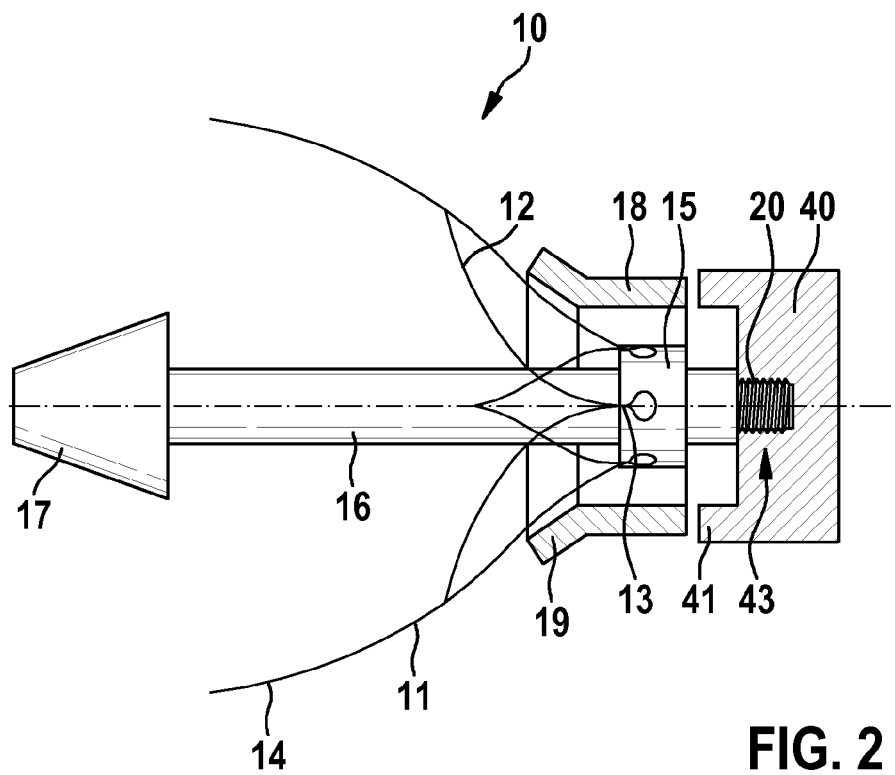
FIG. 2 shows a cross-sectional view of a second exemplary embodiment of an implant according to the invention.

In order to prevent the second shaft 18 from falling out of the main structure 11 in the proximal direction, a cover 40 is additionally provided in the second embodiment of an implant according to the invention shown in FIG. 2 and preferably prevents displacement of the second shaft 18 in the proximal direction by means of an annular portion 41, which protrudes in the distal direction and is arranged opposite the second shaft 18. The cover 40 further has a threaded portion 43, which provides an inner thread. The inner thread of the threaded portion 43 can be connected to the outer thread of the first connection portion 20.

Figure 3:
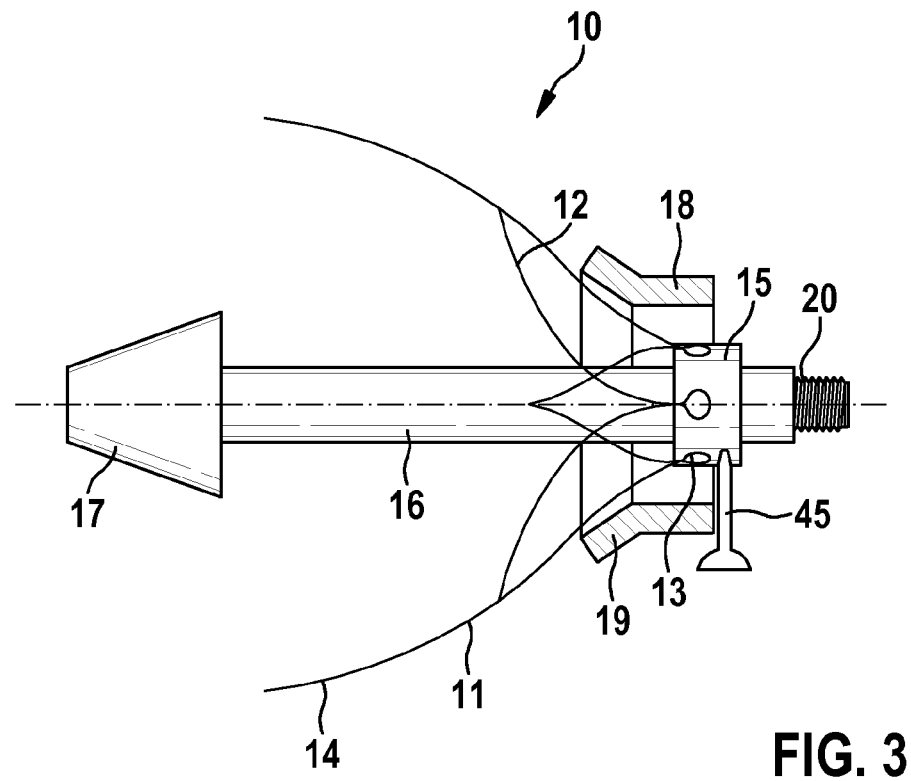
FIG. 3 shows a cross-sectional view of a third exemplary embodiment of an implant according to the invention.

Alternatively and as shown in FIG. 3, a pin 45 protruding in the radial direction can be provided at the proximal end 13 of the main structure 11 and, for example, is fastened in a corresponding opening in the main lattice 11 or the ring 15. This pin 45 prevents displacement of the second shaft 18 in the proximal direction due to its proximal arrangement relative to the second shaft 18.

Figure 4:
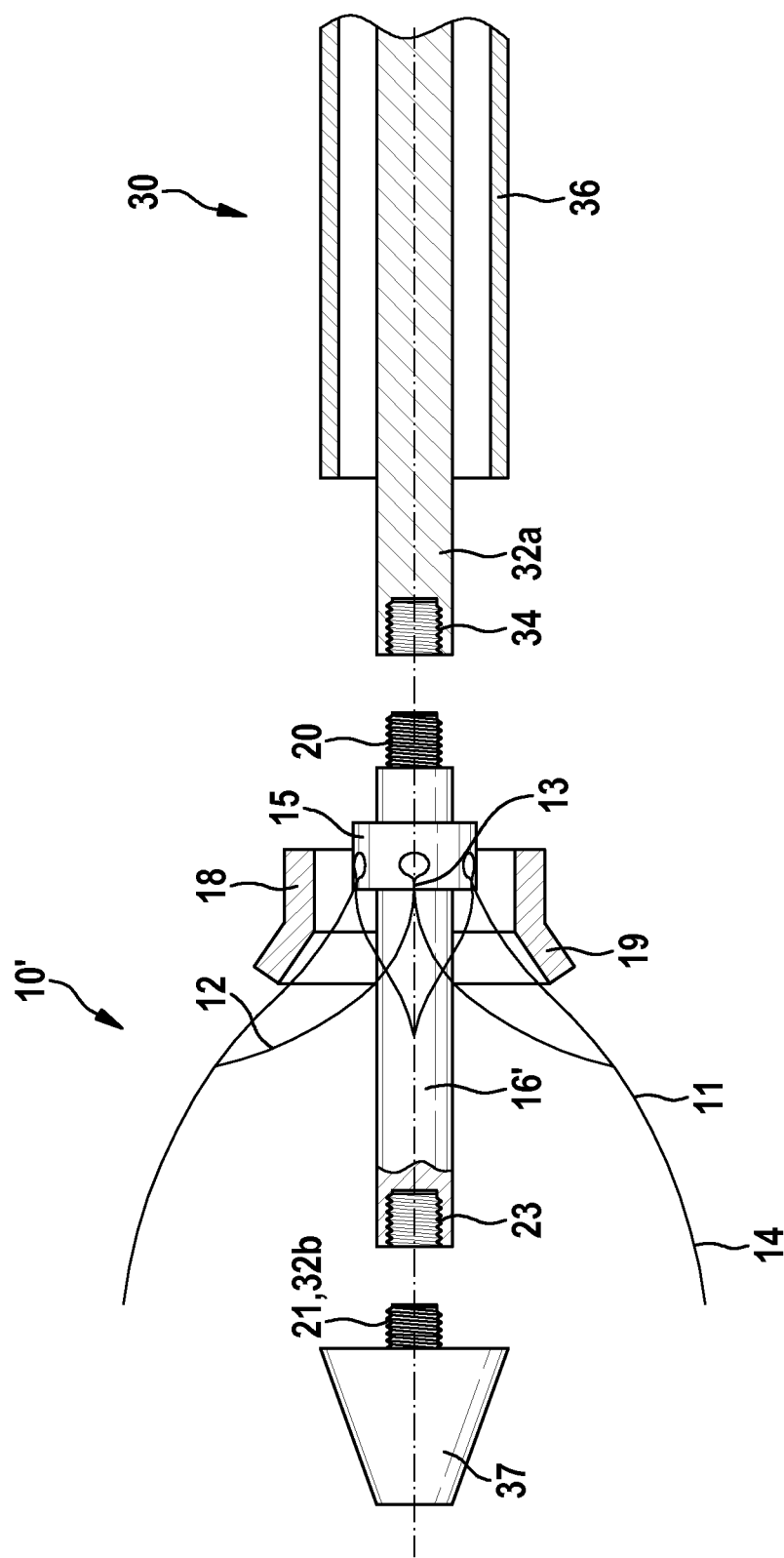
FIG. 4 shows a cross-sectional view of a second exemplary embodiment of a system according to the invention with a fourth exemplary embodiment of an implant according to the invention.

FIG. 4 shows the second exemplary embodiment of a system according to the invention, which corresponds substantially in terms of design to the first exemplary embodiment illustrated in FIG. 1. However, as shown in FIG. 4, the inner shaft is formed in two parts, with a proximal first part 32a and a distal second part 32b. The second part 32b of the inner shaft also contains a conical portion 37, which forms the catheter tip after assembly of the system. The first shaft 16 of the implant according to the invention accordingly has a second connection portion 23, which for example contains an inner thread. At its proximal end, the second part 32b of the inner shaft accordingly provides a connection portion 21 with an outer thread. Alternatively, the second part 32b of the inner shaft of the catheter 30 can also be connected to the first shaft 16' by means of a bayonet closure or by means of adhesive for example.

This exemplary embodiment is particularly advantageous if the second shaft 18 is dimensioned such that it cannot be slid over the catheter tip (conical portion 37). In the exemplary embodiment illustrated in FIG. 4, the main structure 11 with the valvular cusp 12 is accordingly first pre-crimped by means of the second shaft 18, and the outer shaft 36 is then slid over the main lattice 11. The second part 32b of the inner shaft is then connected to the first shaft 16' of the heart valve stent 10 as described above.

Figure 5:
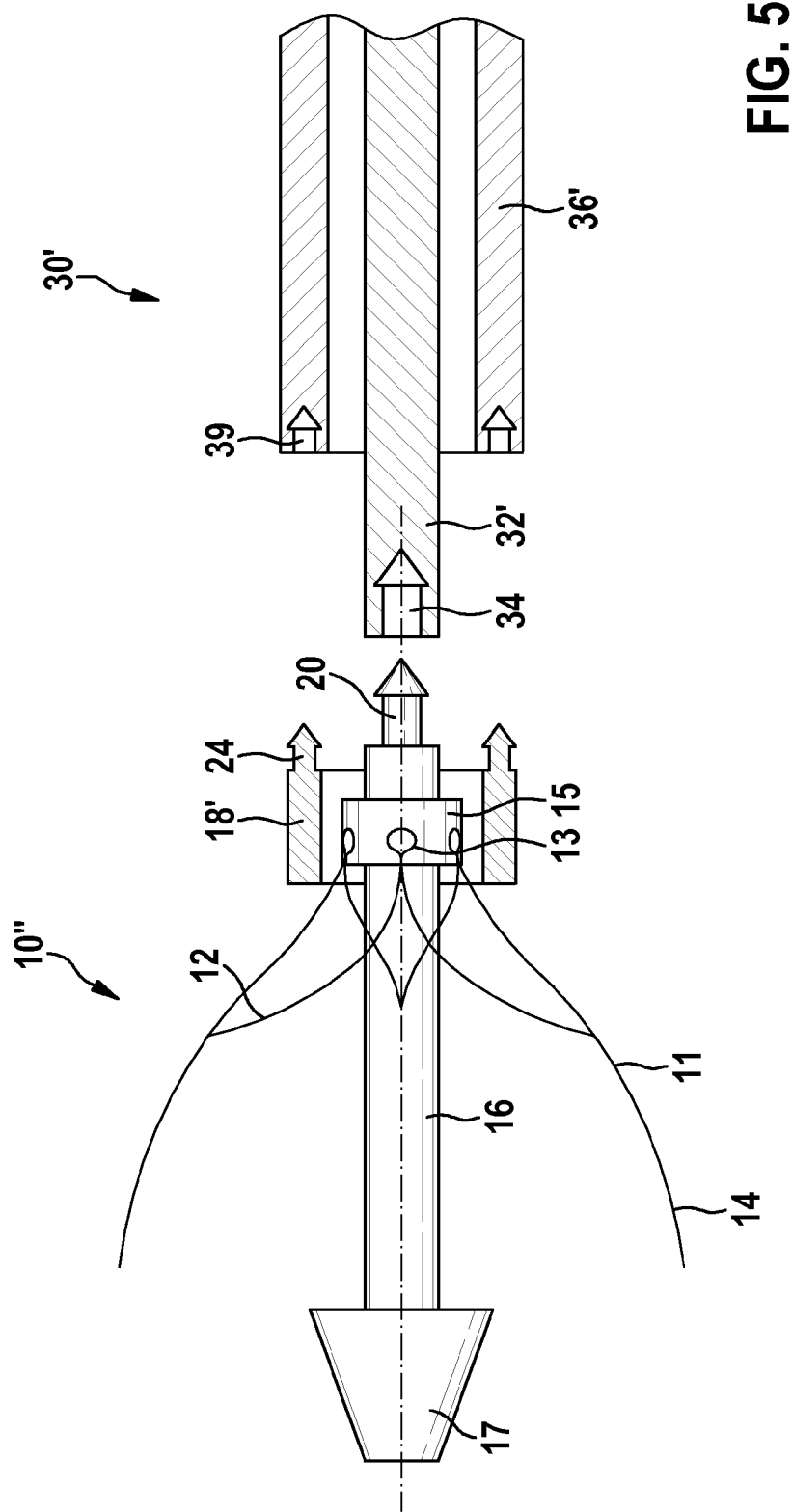
FIG. 5 shows a cross-sectional view of a third exemplary embodiment of a system according to the invention with a fifth exemplary embodiment of an implant according to the invention, and FIG. 6 likewise shows a cross-sectional view of a fourth exemplary embodiment of a system according to the invention with a sixth exemplary embodiment of an implant according to the invention.

The third exemplary embodiment illustrated in FIG. 5 of a system according to the invention shows the case in which the second shaft 18' is coupled to the outer shaft 36' and the first shaft 16 is coupled to the inner shaft 32'. The first shaft 16 and the second shaft 18' are initially decoupled from the release unit (catheter) and, after coupling by the doctor, effectively form distal parts of the inner shaft 32' and of the outer shaft 36' and therefore distal parts of the release unit (catheter). In this case, the heart valve stent 10'' does not have to be fixed by a further shaft, but can be fixed by the proximal outer shaft 36'. At its proximal end, the second shaft 18' has a connection portion 24, which can be connected to the distal connection portion 39 of the outer shaft 36'. In addition, the connection portion 20 of the first shaft 16 can be connected to the distal connection portion 34 of the inner shaft 32'.

The exemplary embodiment illustrated in FIG. 6 of a system according to the invention describes a structural solution in which the catheter 30'' has three shafts, namely an inner shaft 32, an outer shaft 36 and a fixing shaft (auxiliary shaft) 47 therebetween. This exemplary embodiment includes the possibility that the proximal end of the heart valve stent 10''' is fixed on the first shaft 16 by the fixing shaft 47, which is decoupled from the release unit, via a mechanism with a non-positive or positive fit.

When the first shaft 16 of the implant 10''' is coupled to the catheter 30'' via a mechanism already described in conjunction with FIG. 1, the fixing shaft 47 is in this case simultaneously coupled to the second shaft 18'' and is connected thereto. When the inner shaft 32 and the auxiliary shaft 47 are coupled, the main lattice 11 is crimped by advancing the outer shaft 36 in the distal direction. The heart valve stent 10''' is fixed at its proximal end on the instrument by the second shaft 18''', and after assembly by the fixing shaft 47, until the doctor releases the fixing, for example once the stent 10''' has been placed in the desired area of the body of the patient to be treated.

This exemplary embodiment is particularly advantageous in terms of the fixing of the stent, since the end of the stent in the curve can no longer spring out from the fixing. As a result, accurate placement of the heart valve stent 10''' is made possible. To fix the heart valve stent, the fixing shaft 47 has, at its distal end, a connection portion 49 that can be coupled to a corresponding connection portion 24' arranged at the proximal end of the second shaft 18'''. In this exemplary embodiment, the second shaft 18''' is formed such that it cannot be displaced in the longitudinal direction, in contrast to the exemplary embodiment explained above.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

LIST OF REFERENCE SIGNS 10, 10', 10'', 10''' heart valve stent
11 main structure
12 valvular cusp
13 proximal end of the main structure 11
14 distal end of the main structure 11
15 ring
16, 16' first shaft
17 conical portion of the first shaft 16
18, 18', 18'', 18''' second shaft
19 conical portion of the second shaft 18
20 first connection portion of the first shaft 16, 16'
21 connection portion of the second part 32b of the inner shaft
23 second connection portion of the first shaft 16'
24, 24' connection portion of the second shaft 18', 18'', 18'''
30, 30', 30'' catheter
32, 32' inner shaft
32a first part of the inner shaft
32b second part of the inner shaft
34 first connection portion of the inner shaft 32
36, 36' outer shaft
37 conical portion of the second part 32b of the inner shaft 32
39 connection portion of the outer shaft 36'
40 cover
41 protruding ring
43 connection portion of the cover 40
45 pin
47 fixing shaft
49 connection portion of the fixing shaft 47

What is claimed is:
1. An implant preassembly comprising:
an intraluminal endoprosthesis that can adopt a compressed state and an expanded state;
a first shaft over which a proximal end of the endoprosthesis is arranged in the compressed state, wherein the first shaft has a first connection portion configured for connection to an inner shaft of a catheter and a second connection portion at a distal end for connection with a conical portion; and a second shaft slidably positioned over the first shaft that slides distally to compress a distal portion of the endoprosthesis independent of connection of the implant preassembly to the catheter.

2. The implant preassembly according to claim 1, characterized in that the second shaft is arranged at a proximal end of the first shaft so as to surround the proximal end of endoprosthesis in the compressed state.

3. The implant preassembly according to claim 2, further comprising a means for fixing the second shaft in the proximal direction thereby preventing removal of the second shaft from the first shaft proximally prior to connection to the catheter.

4. The implant preassembly according to claim 2, characterized in that the second shaft has a conical portion arranged at the distal end of the second shaft.

5. The implant according to claim 2, characterized in that the second shaft has a connection portion configured for connection to an outer shaft of the catheter or a fixing shaft positioned between the inner shaft and outer shaft of the catheter.

6. An implant system for introducing an intraluminal endoprosthesis into a bodily cavity, the implant system comprising the implant preassembly according to claim 1 and a catheter comprising an inner shaft and an outer shaft, wherein the inner shaft of the catheter has a connection portion at a distal end configured for connection to the first connection portion.

7. The implant system according to claim 6, characterized in that the outer shaft of the catheter or a fixing shaft of the catheter has a connection portion arranged at a respective distal end, with which the outer shaft or the fixing shaft respectively can be connected to the second shaft of the implant preassembly.

8. The implant system according to claim 6, characterized in that the inner shaft of the catheter is formed in two parts, wherein the first part connects to the first connection portion and a second part connects to a distal portion of the first shaft.

9. A method for producing an implant system according to claim 8, comprising:
providing the preassembly with the endoprosthesis compressed at a proximal end and surrounded by the second shaft, wherein the preassembly is remote from the catheter; and
connecting the first part of the inner shaft to the first connection portion of the first shaft and connecting the second part of the inner shaft to the distal portion of the first shaft.

10. A method for producing an implant system according to claim 6, comprising:
providing the preassembly with the endoprosthesis compressed at a proximal end and surrounded by the second shaft, wherein the preassembly is remote from the catheter; and
connecting the preassembly to the catheter.

11. The method according to claim 10, wherein the step of connecting the preassembly to the catheter comprises connecting the first shaft to the inner shaft of the catheter and connecting the second shaft to either the outer shaft or fixing shaft of the catheter.

12. The implant preassembly according to claim 1, wherein the endoprosthesis is a heart valve stent.

13. An implant preassembly comprising:
an intraluminal endoprosthesis that can adopt a compressed state and an expanded state;
a first shaft over which a proximal end of the endoprosthesis is arranged in the compressed state, wherein the first shaft has a first connection portion configured for connection to an inner shaft of a catheter;
a second shaft slidably positioned over the first shaft that slides distally to compress a distal portion of the endoprosthesis independent of connection of the implant preassembly to the catheter; and
a ring comprising recesses fixed to the first shaft, wherein the proximal end of the endoprosthesis is attached to the ring.

14. The implant preassembly according to claim 13, wherein the second shaft is configured for connection to an outer shaft of a catheter.

15. The implant preassembly according to claim 13, further comprising a conical portion at a distal end of the first shaft.

16. The implant preassembly according to claim 13, further comprising a pin or a cover that prevents displacement of the second shaft proximally.

17. An implant preassembly comprising:
an intraluminal endoprosthesis that can adopt a compressed state and an expanded state;
a first shaft over which a proximal end of the endoprosthesis is arranged in the compressed state, wherein the first shaft has a first connection portion configured for connection to an inner shaft of a catheter;
a second shaft slidably positioned over the first shaft that slides distally to compress a distal portion of the endoprosthesis independent of connection of the implant preassembly to the catheter; and
a ring fixed to the first shaft and attached to the proximal end of the endoprosthesis.

* * * * *